(12) United States Patent
Awad et al.

(10) Patent No.: US 9,623,067 B1
(45) Date of Patent: Apr. 18, 2017

(54) METHOD OF PREPARING DATE PALM SEED NANOPARTICLES

(71) Applicant: KING SAUD UNIVERSITY, Riyadh (SA)

(72) Inventors: Manal Ahmed Gasmelseed Awad, Riyadh (SA); Ebtesam Mohammed Al Olayan, Riyadh (SA); Hany Mohamed Yehia, Riyadh (SA); Khalid Mustafa Osman Ortashi, Riyadh (SA); Hatem Salama Mohamed Ali, Riyadh (SA); Manal Fawzy Elkhadragy, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 15/333,143

(22) Filed: Oct. 24, 2016

(51) Int. Cl.
*A61K 36/889* (2006.01)

(52) U.S. Cl.
CPC .................................. *A61K 36/889* (2013.01)

(58) Field of Classification Search
CPC .................................................... A61K 36/889
See application file for complete search history.

(56) References Cited

U.S. PATENT DOCUMENTS

| 8,992,670 B1* | 3/2015 | Vohra | B01D 15/265 |
|---|---|---|---|
| | | | 502/400 |
| 2011/0143001 A1 | 6/2011 | Cohen et al. | |
| 2016/0312100 A1* | 10/2016 | Amanullah | C09K 8/08 |

FOREIGN PATENT DOCUMENTS

IN  201333  2/2007

* cited by examiner

*Primary Examiner* — Mark V Stevens
(74) *Attorney, Agent, or Firm* — Richard C. Litman

(57) ABSTRACT

A method of preparing nanoparticles of date palm seeds comprises providing date seed powder; mixing the date seed powder with an acid solution to produce date palm seed nanoparticles; and isolating the date palm seed nanoparticles. A method of controlling the growth or proliferation of bacteria can include administering an effective amount of the date palm seed nanoparticles synthesized according to the present method to a site of bacterial activity.

5 Claims, 2 Drawing Sheets

METHOD OF PREPARING DATE PALM SEED NANOPARTICLES

BACKGROUND OF THE INVENTION

1. Field of the Invention

The present invention relates generally to nanoparticle synthesis, and particularly, to a method of preparing date palm seed nanoparticles.

2. Description of the Related Art

Nanoparticles exhibit completely new or improved properties compared to their corresponding bulk materials. Because of their size, catalytic property, ability to deliver drug, increased efficacy, and decreased toxicity, nanotechnology finds applications in various fields including healthcare, defense and day-to-day life.

The date palm (*Phoenix dactylifera* L.) plays an important social, environmental, and economic role for many people living in arid and semiarid regions of the world. Fruits of the date palm are very commonly consumed in many parts of the world and are considered a vital component of the diet in most Arab countries (AlFarsi and Lee 2008). Date palm fruits have demonstrated many medicinal properties when consumed either alone or in combination with other herbs. In recent years, an explosion of interest in the numerous health benefits of the date fruit had led to many in vitro and animal studies as well as the identification and quantification of various classes of phytochemicals.

Thus, a method of producing nanoparticles from date palm seed thereby solving the aforementioned problems is desired.

SUMMARY OF THE INVENTION

A method of preparing nanoparticles of date palm seeds comprises providing date palm seed powder; mixing the date palm seed powder with an acid solution at a stirring speed of about 1000 rpm and a temperature of about 30° C. to produce date palm seed nanoparticles; and isolating the date palm seed nanoparticles.

A method of destroying bacteria and/or inhibiting bacterial growth can include the step of administering an effective amount of the date palm seed nanoparticles synthesized according to the present method to a site of bacterial activity.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A method of preparing nanoparticles of date palm seeds (also referred to as kernels or pits) can include providing date palm seed powder; mixing the date palm seed powder with an acid solution under a stirring speed of about 1000 rpm at a temperature of about 30° C. to produce date palm seed nanoparticles; and isolating the date palm seed nanoparticles by conventional methods. The acid solution can include about 20 ml to about 50 ml of 38% hydrochloric acid. The date palm seed nanoparticles can be isolated by filtration using a Milipore filter having a pore size of about 220 nm. Alternatively, the date palm seed nanoparticles can be isolated by centrifugation for about 15 minutes at a rotation speed of about 9000 rpm. The date palm seed nanoparticles prepared according to the present method can have an average particle size ranging from about 1 nm to about 220 nm. The nanoparticles can be spherical, spheroidal, elongated/spherical, rod-shaped, and/or faceted shaped.

The date palm seed powder can be prepared by soaking the seeds in water, drying the seeds, and then grinding the seeds. The seeds can be ground in a heavy-duty grinder and passed through screens of about 1 mm to about 2 mm. Accordingly, the powder can have a particle size of about 1 mm to about 2 mm or less.

The date palm seed nanoparticles can be used destroy microorganisms or inhibit the growth of microorganisms. Specifically, the date palm seed nanoparticles synthesized according to the present method can demonstrate bactericidal and/or bacteriostatic activity. For example, an effective amount of the date palm seed nanoparticles can be administered to a site of bacterial infection to control the proliferation of bacteria, e.g., destroy bacteria and/or inhibit bacterial growth. The effective amount can be about 1.5 M of the date palm seed nanoparticles in solution. The bacteria can include gram positive and/or gram negative bacteria.

The present method of preparing date palm seed nanoparticles is a simple, cost effective, and non-toxic method, which can be easily scaled up for large scale synthesis. The nanoparticles prepared from date palm seed as described herein can be highly efficient against bacteria associated with food poisoning, as well as other bacteria and microorganisms.

The following examples will further illustrate the process of preparing the date palm seed nanoparticles and their use as antibacterial agents.

EXAMPLE 1

Synthesis of Date Seed Powder

Date seeds were soaked in water, washed to free any adhering date flesh, and then air-dried. Their relative percentage weight compared to the weight of the fresh fruit was about 10.1% for the Sukkari variety. The seeds were further dried in an air oven at 60° C. The dried date palm seeds were ground in a heavy-duty grinder and passed through 1-2 mm screens to produce date palm seeds flour or date-pits powder. The powder was then kept in the freezer at −20° C. until used.

EXAMPLE 2

Preparation of Date Seeds Nanoparticles

Figure 1A:
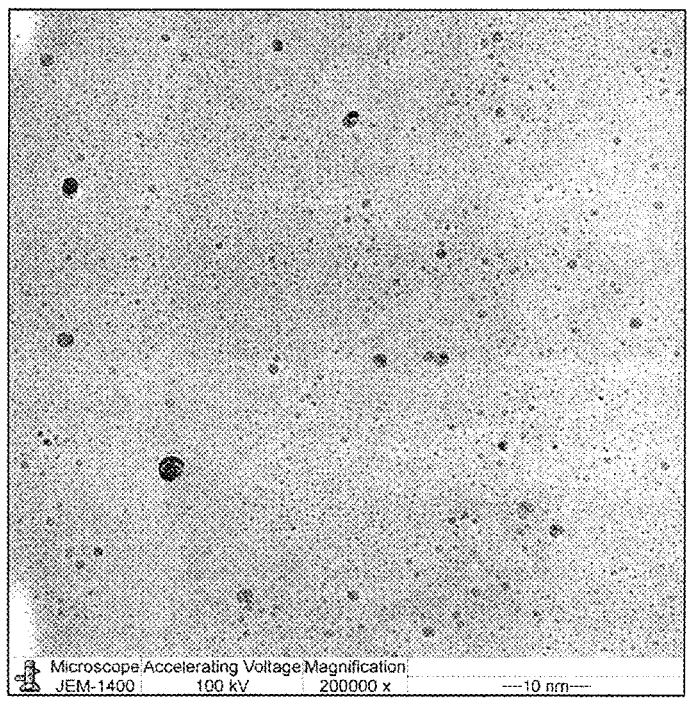
FIGS. 1A-1B show the transmission electron microscopy (TEM) image of date palm seed (*Phoenix dactylifera* L.) nanoparticles synthesized by the inventive method.
Figure 1B:
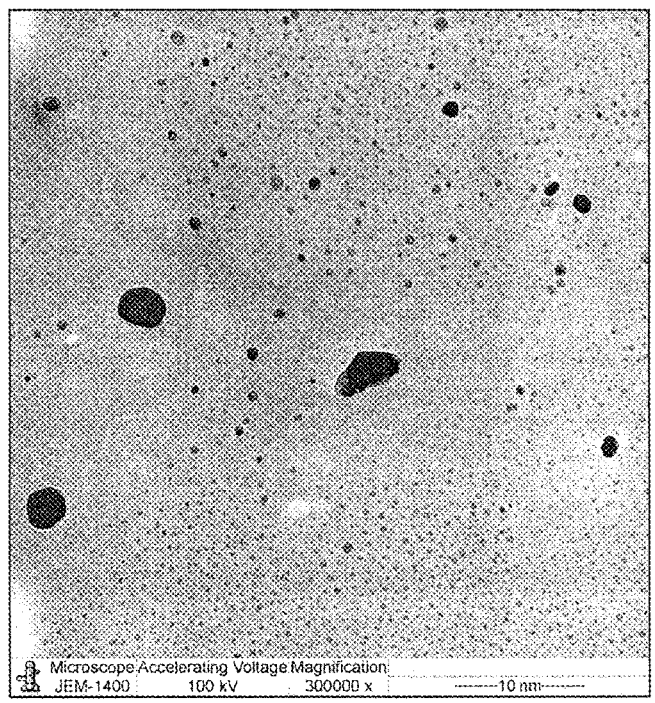
Figure 2:
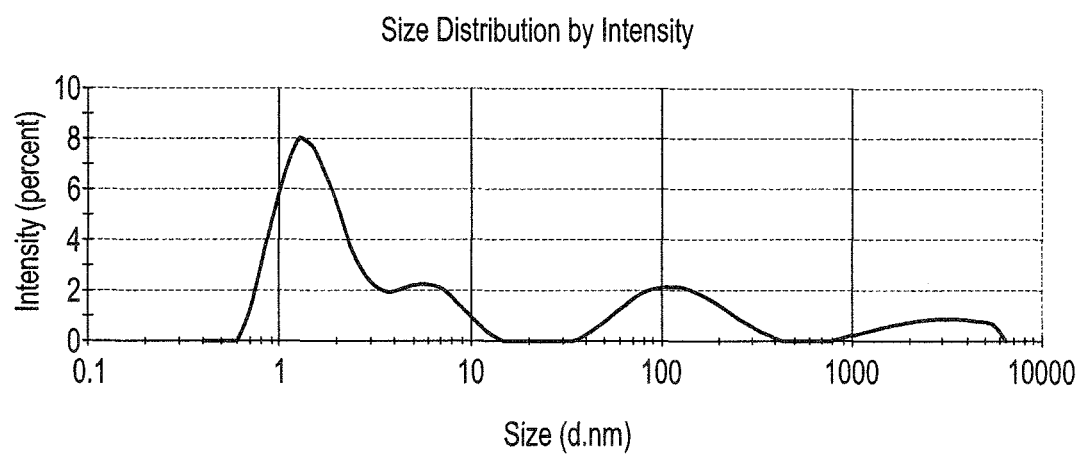
FIG. 2 is a plot of the average particles size of date palm seed (*Phoenix dactylifera* L.) nanoparticles synthesized by the present method.

About 5 g of date palm seed powder was weighed out and poured into a flask including 20-50 mL of 38% hydrochloric acid solution. The flasks were kept under stirring at a speed of 1000 rpm at a temperature of 30±2° C. The date palm seed nanoparticles were filtered through a Millipore filter having a pore size of 220 nm. Alternately, the solution was centrifuged at about 9000 rpm for about 15 minutes to isolate the date palm seed nanoparticles. The nanoparticles were characterized by transmission electron microscopy (JEM-1011, JEOL, Japan). The size of the synthesized nanoparticles was analyzed through Zetasizer, Nano series, HT Laser, ZEN3600 (Molvern Instrument, UK). FIGS. 1A-1B show transmission electron microscopy (TEM) images of the date palm seed (*Phoenix dactylifera* L.) nanoparticles. The particle sizes vary from about 1 nm to about 220 nm. FIG. 2 is a graph showing average particles size of date palm seed (*Phoenix dactylifera* L.) nanoparticles synthesized by the inventive method described herein.

EXAMPLE 3

Agar Well Diffusion Method

The antibacterial activity for nanoparticles was determined using agar well diffusion method. Bacterial concentrations were prepared for each bacteria in normal Ringlers solution at a concentration of 108/ml. The wells were made in Muller Hinton agar by using a cork borer size 8 mm in diameter. Plates were cultured by using a small swab of each bacteria. 100 µl of nanoparticles was introduced into the wells. The inoculated plates were incubated at 37° C. for 24 hrs. Date seed nanoparticles prepared as described in Example 2 and date seed extract were tested on the various strains. Pure methanol was used as control for all of the tested strains. The bacterial strains tested included: *Leclercia adecarboxylat; Enterobacter aerogenes; B. subtilis; E. coli; Enterobacter aerogenes*; and *Listeria monocytogenes*. All bacterial strains were detrimentally affected by date seed nanoparticles more than date seed extract and methanol.

It is to be understood that the present invention is not limited to the embodiments described above, but encompasses any and all embodiments within the scope of the following claims.

We claim:

1. A method of preparing date palm seed nanoparticles, comprising: providing date palm seed powder; mixing the date palm seed powder with an acid solution comprising hydrochloric acid at a temperature of about 30° C., the mixing including stirring the date palm seed powder and the acid solution at a speed of about 1000 rpm to produce date palm seed nanoparticles; and isolating the date palm seed nanoparticles; wherein the date palm seed nanoparticles exhibit a reduced size as compared to the particles of the date palm seed powder.

2. The method of preparing date palm seed nanoparticles according to claim 1, wherein the acid solution includes about 38% hydrochloric acid.

3. The method of preparing date palm seed nanoparticles according to claim 1, wherein the date palm seed nanoparticles are isolated by filtration using a Millipore filter having a pore size of about 220 nm.

4. The method of preparing date palm seed nanoparticles according to claim 1, wherein the date palm seed nanoparticles are isolated by centrifugation for about 15 minutes at a rotation speed of about 9000 rpm.

5. The method of preparing date palm seed nanoparticles according to claim 1, wherein the date palm seed nanoparticles have an average particle size ranging from about 1 nm to about 220 nm.

* * * * *